US009778168B2

(12) United States Patent
Davis et al.

(10) Patent No.: US 9,778,168 B2

(45) Date of Patent: Oct. 3, 2017

(54) COATING MONITOR FOR EVALUATING THE EFFECTIVENESS OF PROTECTIVE COATINGS

(75) Inventors: Guy D. Davis, Baltimore County, MD (US); Ryan C. Dunn, Charlottesville, VA (US); Robert A. Ross, Charlottesville, VA (US)

(73) Assignee: ElectraWatch, Inc., Charlottesville, VA (US)

( * ) Notice: Subject to any disclaimer, the term of this patent is extended or adjusted under 35 U.S.C. 154(b) by 823 days.

(21) Appl. No.: 13/376,424

(22) PCT Filed: Jun. 8, 2010

(86) PCT No.: PCT/US2010/037686

§ 371 (c)(1),
(2), (4) Date: Dec. 6, 2011

(87) PCT Pub. No.: WO2010/144387

PCT Pub. Date: Dec. 16, 2010

(65) Prior Publication Data

US 2012/0081136 A1 Apr. 5, 2012

Related U.S. Application Data

(60) Provisional application No. 61/185,835, filed on Jun. 10, 2009.

(51) Int. Cl.

*G01R 27/08* (2006.01)

*G01N 17/02* (2006.01)

(Continued)

(52) U.S. Cl.

CPC ............ *G01N 17/02* (2013.01); *G01N 17/00* (2013.01); *G01N 17/04* (2013.01); *G01N 27/00* (2013.01); *G01N 27/02* (2013.01)

(58) Field of Classification Search

CPC ........ G01N 17/02; G01N 17/04; G01N 17/00; G01N 27/02

USPC .................................................. 324/700, 693

See application file for complete search history.

(56) References Cited

U.S. PATENT DOCUMENTS

| | | | |
|---|---|---|---|
| 4,380,763 | A | 4/1983 | Peart et al. |
| 5,243,298 | A | 9/1993 | Runner |

(Continued)

OTHER PUBLICATIONS

Koch, Gerhardus, H; Brongers, Michiel, P. H.; Thompson, Neil G.; Virmani, Y. Paul; and Payer, Joe H.; "Corrosion Costs and Preventive Strategies in the United States;" Report by CC Technologies Laboratories, Inc. to Federal Highway Administration (FHWA), Office of Infrastructure Research and Development; Report FHWA-RD-01-156; Sep. 2001.

(Continued)

*Primary Examiner* — Amy He

(74) *Attorney, Agent, or Firm* — Paul A. Bell

(57) ABSTRACT

The coating monitoring system is based on electrochemical impedance spectroscopy (EIS). The system consists of one or more compact and rugged mini-potentiostat modules coupled to one or more electrodes mounted on top of the paint coating of the structure being monitored. The electrodes and modules can be coated with a topcoat if desired. Alternatively, they may be mounted only temporarily to the structure for spot inspection. They periodically report to a laptop. Communications may be implemented using a wireless protocol. The units may be battery powered with an estimated battery lifetime of up to ten years, depending on the frequency of measurement and interrogation Alternative power supplies may be used to replace or supplement the battery to allow extended battery lifetime. Moisture, humidity, or other sensors may be incorporated into the coating monitor.

10 Claims, 9 Drawing Sheets

(51) Int. Cl.

| | |
|---|---|
| ***G01N 17/04*** | (2006.01) |
| ***G01N 27/00*** | (2006.01) |
| ***G01N 17/00*** | (2006.01) |
| ***G01N 27/02*** | (2006.01) |

(56) References Cited

U.S. PATENT DOCUMENTS

| | | | | |
|---|---|---|---|---|
| 5,299,271 | A | 3/1994 | Hildebrand | |
| 5,306,414 | A | 4/1994 | Glass et al. | |
| 5,310,470 | A | 5/1994 | Agarwala et al. | |
| 5,338,432 | A | 8/1994 | Agarwala et al. | |
| 5,437,773 | A | 8/1995 | Glass et al. | |
| 5,859,537 | A | 1/1999 | Davis et al. | |
| 6,054,038 | A | 4/2000 | Davis et al. | |
| 6,313,646 | B1 | 11/2001 | Davis et al. | |
| 6,328,878 | B1 * | 12/2001 | Davis et al. | 205/776.5 |
| 6,683,463 | B2 | 1/2004 | Yang et al. | |
| 6,809,506 | B2 | 10/2004 | Thomas, III et al. | |
| 6,911,828 | B1 * | 6/2005 | Brossia et al. | 324/649 |
| 7,088,115 | B1 | 8/2006 | Glenn et al. | |
| 7,228,017 | B2 | 6/2007 | Xia et al. | |
| 7,313,947 | B2 | 1/2008 | Harris et al. | |
| 7,477,060 | B2 | 1/2009 | Yu et al. | |
| 2002/0057097 | A1 * | 5/2002 | Kelly et al. | 324/700 |
| 2004/0149594 | A1 * | 8/2004 | Eden | 205/775.5 |
| 2008/0150555 | A1 | 6/2008 | Wang et al. | |

OTHER PUBLICATIONS

Davis, G.D.; Dacres, C.M.; and Krebs, L.A.; "In-Situ Corrosion Sensor for Coating Testing and Screening," Materials Performance 39(2), 46 (2000).

Davis, G.D.; Dacres, C.M.; and Krebs, L.A.; "EIS-Based In-Situ Sensor for the Early Detection of Coating Degradation and Substrate Corrosion," Corrosion2000, Paper 275 (NACE, Houston, TX, 2000).

Green, J; Jones, M; Bailey, T.; and Perez, I.; "Process Control and Sensors for Manufacturing," R.H. Bossi and D.M. Pepper, ed., (SPIE—The International Society for Optical Engineering, Bellingham, WA, 1998), p. 28.

Agarwala, V.S.; Corrosion96, Paper 632, NACE, Houston, TX, 1996.

Kelly, R.G.; Yuan, J.; Jones, S. H.; Blanke, W.; Alor, J.H.; Wang, W.; Batson, A.P.; Wintenberg, A.; and Clemeña, G. G. ; Corrosion97, Paper 294, NACE, Houston, TX 1996.

Zhang, J. and Frankel, G.S. In Nondestructive Characterization of Materials in Aging Systems, MRS Symp. Series,vol. 503.

Johnson. R.E. and Agarwala, V. S. ; Corrosion97, Paper 304, NACE, Houston, TX, 1997.

Stephenson, L.D.; Kumar, A.; Hale, J. and Murray, J.N.; "Sensor System for Measurement of Corrosion Under Coatings," Mater. Perf. 48(5) 36 (May 2009).

Davis, G.D.; Ross, Robert A.; Raghu, Surya; Coating Health Monitoring System for Army Ground Vehicles. Paper 07230 Corrosion2007 NACE.

Davis, G.D.; Raghu, Surya; Carkhuff, Bliss G.; Garra, Fernando; Srinivasan, Rengaswamy; and Phillips, Terry E.; Corrosion Health Monitor for Ground Vehicles, Proceedings 2005 Tri-Services Conference on Corrosion, 2005 (Orlando, Florida).

Coating Health Monitor (CHM) Document on ElectraWatch, Inc. Website., posted sometime after Aug. 23, 2009.

* cited by examiner

COATING MONITOR FOR EVALUATING THE EFFECTIVENESS OF PROTECTIVE COATINGS

CROSS-REFERENCE TO RELATED APPLICATIONS

This application claims the benefit under 35 U.S.C. 119(e) of prior U.S. Provisional application 61/185,835 filed on Jun. 10, 2009.

SEQUENCE LISTING

Not Applicable

BACKGROUND OF THE INVENTION

The invention involves a compact, rugged coating monitor. Corrosion is a wide-spread problem that affects nearly all industry and government sectors. A recent report determined that the direct cost of corrosion in the United States to be 3.1% of the Gross Domestic product (GDP) [Gerhardus H. Koch, Michiel P. H. Brongers, Neil G. Thompson. Y. Paul Virmani, Joe H. Payer, "Corrosion Costs and Preventive Strategies in the United States," Report by CC Technologies Laboratories, Inc. to Federal Highway Administration (FHWA), Office of Infrastructure Research and Development, Report FHWA-RD-01-156, September 2001]. This corresponds to $300B annually or $1000 per person. This figure includes only the direct costs (e.g., corrosion prevention, corrosion inspection, and replacement or refurbishment of corroded structures). The indirect costs (e.g., lost productivity, taxes, and overhead) were conservatively estimated to be equal to the direct costs.

Paint coatings are the primary means of corrosion protection for most structures and they can be very effective. However, paint coatings are only temporary; they weather, absorb moisture, blister, become scratched or undergo other mechanical damage. Even fresh paint coatings can exhibit pinholes, holidays, or other coating defects that can adversely affect corrosion protection. Thus, there is a need for corrosion sensors to assess the health and effectiveness of paint coatings, especially on critical structures and equipment.

Although many corrosion sensors have been proposed and developed [G. D. Davis, C. M. Dacres, and L. A. Krebs, "In-Situ Corrosion Sensor for Coating Testing and Screening," *Materials Performance* 39(2), 46 (2000); G. D. Davis, C. M. Dacres, and L. A. Krebs, "EIS-Based In-Situ Sensor for the Early Detection of Coating Degradation and Substrate Corrosion," *Corrosion*2000, Paper 275 (NACE, Houston, Tex., 2000); G. D. Davis, C. M. Dacres, and L. A. Krebs, "EIS-Based In-Situ Sensor for the Early Detection of Coating Degradation and Substrate Corrosion," *Corrosion*2000, Paper 275 (NACE, Houston, Tex., 2000); J. Green, M. Jones, T. Bailey, and I. Perez, *Process Control and Sensors for Manufacturing*, R. H. Bossi and D. M. Pepper, ed., (SPIE—The International Society for Optical Engineering, Bellingham, Wash., 1998), p. 28; V. S. Agarwala, *Corrosion*96, Paper 632, NACE, Houston, Tex., 1996; R. G. Kelly, J. Yuan, S. H. Jones, W. Blanke, J. H. Alor, W. Wang, A. P. Batson, A. Wintenberg, and G. G. Clemena, *Corrosion*97, Paper 294, NACE, Houston, Tex. 1996; J. Zhang and G. S. Frankel, in *Nondestructive Characterization of Materials in Aging Systems, MRS Symp. Series*, Vol. 503, R. Crane, J. Achenbach, S. Shah, T. Matikas, P. Khuri, and L. Yakub, eds., (Materials Research Society, Warrendale, Pa., 1998), p. 15; R. E. Johnson and V. S. Agarwala, *Corrosion*97, Paper 304, NACE, Houston, Tex., 1997; L. D. Stephenson, A. Kumar, J. Hale, and J. N. Murray, "Sensor System for Measurement of Corrosion Under Coatings," *Mater. Perf.* 48(5) 36 (May 2009)], many are not suitable for monitoring coating health. A major disadvantage of many of these, such as galvanic couple sensors (U.S. Pat. No. 5,306,414, U.S. Pat. No. 5,437,773, U.S. Pat. No. 5,243,298, U.S. Pat. No. 6,809,506, U.S. Pat. No. 4,380,763, U.S. Pat. No. 6,683,463, U.S. Pat. No. 7,313,947, U.S. Pat. No. 5,338,432, and U.S. Pat. No. 5,310,470) and many fiber optic corrosion sensors (U.S. Pat. No. 5,299,271, U.S. Pat. No. 7,228,017), is that they are more properly considered corrosivity sensors; that is, they detect degradation of a sensor element and not degradation of the structure of interest. As such, they measure only how corrosive the environment is and provide no direct information on the condition of the coating or the structure. Furthermore, they are consumed and have a limited lifetime and can provide no information concerning any environmental degradation prior to installation. A second disadvantage of many sensors is that they need to be embedded into the structure. This limits them to new construction and poses important issues on the effect of the sensor on structure properties and data acquisition/transfer. These sensors cannot inspect existing structures and cannot be replaced if damaged or past their useful lifetime. The electrochemical impedance sensor approach developed here has neither of these critical disadvantages. The technology is suitable for determining coating health and detection of damage under paint coatings.

The coating monitor of the present invention is a compact and rugged integrated detection and reporting system that uses electrochemical impedance spectroscopy (EIS)-based corrosion sensors and mini-potentiostat elements. Corrosion sensors for military and civilian applications are most useful when the devices do not require invasion into the coating being monitored for protection or embedding within the structure. The coating monitor of the present invention uses conductive tape sensors to allow EIS measurements to be taken without remote electrodes. Using that engineering approach allows the coating monitor to be applied at times and in locations needed with the flexibility to remove it without decommissioning the structure or vehicle to which it is attached, or removing part of the monitored structure. Its small size and ruggedness are a huge commercial advantage. A patent search found a number of patent documents that approached some aspect of coating monitoring from an EIS sensor perspective. Documents of particular note include U.S. Pat. No. 7,477,060 ('060 Yu, S. Y. et al) and published application US20080150555 ('555 Wang, D. et al), which has its sensors on the surface or embedded in a flexible substrate integrated into the monitored structure, and U.S. Pat. No. 6,911,828 ('828 Brossia, C. S. et al), which has arrays of sensor pins in contact with the structure's coating. Also of interest is U.S. Pat. No. 7,088,115 ('115 Glenn, D. F. et al), for an EIS system designed specifically for uncured concrete.

With respect to the '060 patent, the specification discusses the feasibility of attaching the sensors with adhesives but this feature is not included in the claims of the patent. In the published application, '555, an optoelectronic backbone communicates data from the sensors to a control device.

Similarly, the '828 patent describes a sensor array in the form of sensor pins in contact with the coating being monitored and a data interrogation device positioned in proximity to the sensor array.

The '115 patent is directed specifically at detecting defects in uncured concrete before the curing process. It is much more limited in application than the '060 or '828 systems.

The DACCO SCI, INC., portfolio discloses permanent or handheld sensors that use EIS to detect moisture and other changes in coatings U.S. Pat. No. 5,859,537 ('537 Davis, G. D. et al), U.S. Pat. No. 6,054,038 (038 Davis, G. D. et al), U.S. Pat. No. 6,313,646 ('646 Davis, G. D. et al) and U.S. Pat. No. 6,328,878 ('878 Davis, G. D. et al). The '537 patent is directed to an in situ sensor suitable for coated metal structures. The sensor comprises conductive ink and is permanently applied to the topcoat being monitored. The '038 patent teaches the corrosion sensor as a handheld device comprising a metal. The '646 patent teaches the use of two hand-held electrodes to detect moisture absorption, corrosion, and adhesive bond degradation. The '878 patent teaches the use of a pair of conductive foil adhesive tapes, one with a conductive adhesive and one with a nonconductive adhesive, to determine coating or substrate degradation. All of these inventions use a separate bench-top or similar-sized potentiostat to be connected and to acquire the EIS measurements; thus they are not suitable for remote or unattended operation.

An example of a prior art potentiostat would be the Gamry Reference 3000 potentiostat that is 20-cm×23-cm×30-cm and weighs approximately 6 kg. FIG. 1 shows a block diagram of a generic potentiostat 10 comprised of an ac voltage generator 12; a galvanometer 14 to measure the current (magnitude and phase) induced by the said ac voltage; a means 16 to make electrical connection to the specimen being measured; a means 18 to make electrical connection to reference and counter electrodes immersed into an electrolyte along with the specimen; a means 20 to convert the current measurement into an electrochemical impedance measurement (magnitude and phase); and a means for input/output 22.

SUMMARY OF THE INVENTION

A principal objective of the present invention is to provide a compact and rugged coating monitor. The entire coating monitor of the present invention can be attached to the coated structure and left in place for long periods of time. This permits the coating monitor to be secured to the coated structure wherein it can take and store measurement data regarding coating characteristics and transmit these data to a remote receiver at a convenient time.

However, it is not necessary to permanently secure the coating monitor to the structure. The compact nature of the coating monitor of the present invention permits it to be useful in situations where a permanent attachment to the structure is not desirable. For example, a permanently mounted monitor may not be desired for cosmetic reasons. Additionally, in cases such as a fluid flow environment, e.g., an airfoil surface, a permanent monitor could disturb the fluid flow and would not be desirable. In this embodiment, the coating monitor could be removably secured to the structure. A final advantage of this embodiment is the ability to collect coating measurement data from multiple locations on the structure or from multiple structures using a single coating monitor.

An additional objective of the present invention is to provide a coating monitor which can take and store information concerning the coating and also take and store other information of interest such as environmental information, battery life, and other parameters of interest. For example, the electrochemical impedance spectrum of a coated structure may depend on the humidity or surface wetness of the structure. A means to determine the humidity or surface wetness is desirable.

The present invention allows for broad applicability, flexibility in utilizing the coating monitor in various environments without structural compromise and the ability to inspect and evaluate the actual structure regardless of its size. This adaption includes the utilization of a widely accepted and recognized laboratory technique of electrochemical impedance spectroscopy for the investigation of coating deterioration and substrate corrosion.

DETAILED DESCRIPTION

Figure 1:
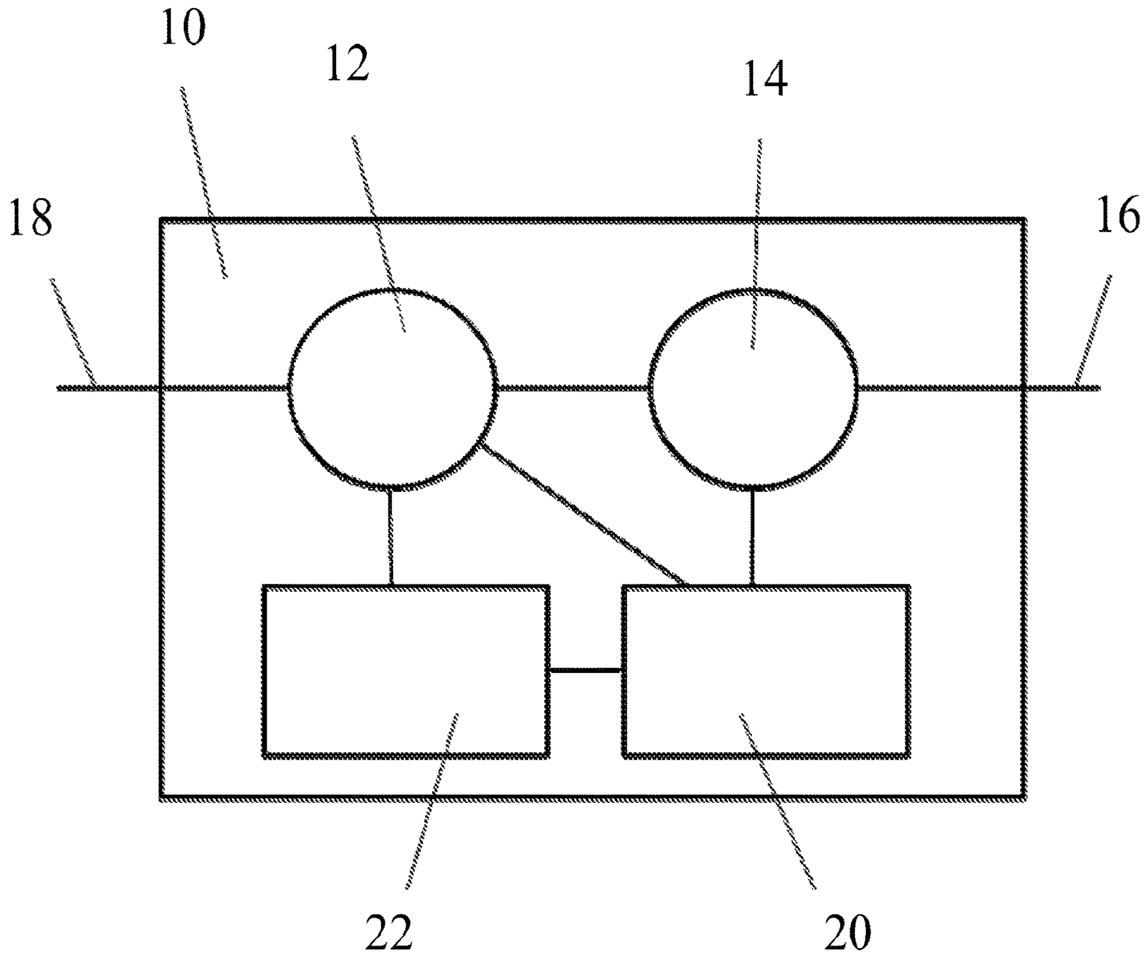
FIG. 1 shows a block diagram of a generic potentiostat.
Figure 2:
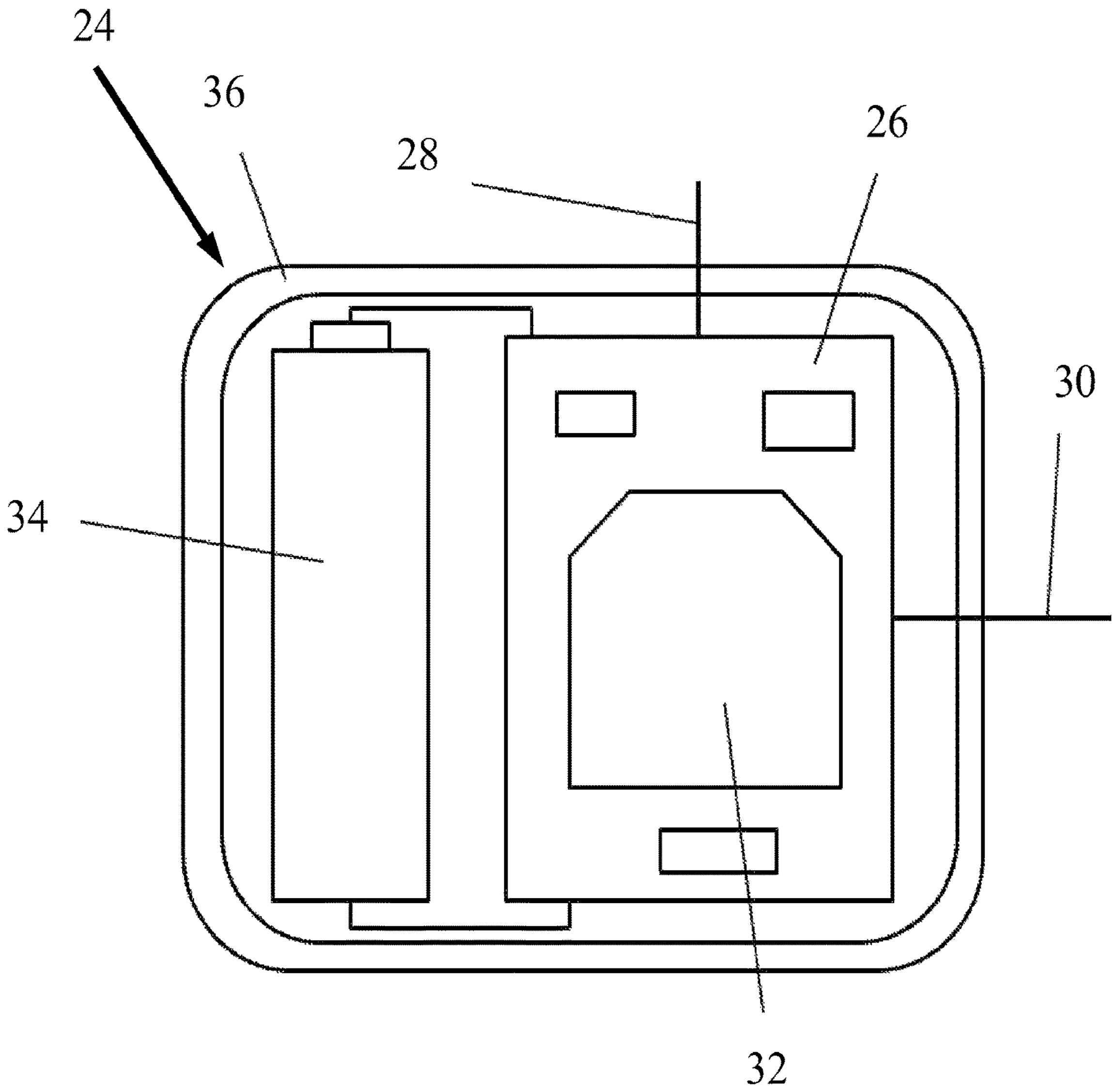
FIG. 2 shows a block diagram of the coating monitor.

FIG. 2 shows a block diagram of a coating monitor 24 comprising a circuit board potentiostat 26 comprising an ac voltage generator operating at one or more frequencies; a galvanometer to measure the current (magnitude and phase) induced by the ac voltage; a means 28 to make measure the current (magnitude and phase) induced by the ac voltage; a means 28 to make electrical connection to the substrate shown in subsequent figures; a means 30 to make electrical connection to the electrode(s) shown in subsequent figures; a means to convert the current measurement into an electrochemical impedance measurement (magnitude and phase); and a transceiver 32 for input/output. The coating monitor is powered by an AA or A battery 34. The entire coating monitor is contained in a compact waterproof casing 36.

Compact waterproof casing 36 has an interior recess with a predetermined length, width and height. As can clearly be seen from the showing of FIG. 2, the predetermined length of the interior recess of casing 36 is slightly more than the length of A or AA battery 34. The predetermined width of the interior recess of casing 36 is also slightly greater than the length of A or AA battery 34 but somewhat greater than the predetermined length. As can be clearly seen from the showing of FIGS. 3, 5 and 6-8, the predetermined height of the interior recess of casing 36 is substantially less than the length of A or AA battery 34. Both A and AA batteries have substantially the same length, approximately 50 mm, thus the predetermined length and width of the interior recess of casing 36 is approximately 50 mm.

The coating monitor of the present invention includes a potentiostat that is designed to provide only the most essential information to assess a coating's effectiveness and thus minimizes its size, weight, complexity, and power consumption. It comprises an ac voltage generator operating at one or more frequencies, preferably a plurality of frequencies below 100 Hz, more preferably a plurality of frequencies below 10 Hz; a galvanometer to measure the current (magnitude and phase) induced by the said ac voltage; one or more electrodes applied to or pressed against a coating; a means to make electrical connection to the substrate and to the electrode(s); a means to convert the current measurement into an electrochemical impedance measurement (magnitude and phase); and an optional clock to provide a timestamp to the data. The coating monitor may comprise distinct components, a hybrid microcircuit or an application specific integrated circuit. The data may be stored internally to the coating monitor or wirelessly transmitted to a computer or other device. Alternatively the data may be outputted to a computer or other device in real time. The coating monitor may have internal battery power or may obtain power via a lead. Other power sources, such as solar cells, vibration energy scavenging, or the like may replace or supplement the battery. Additional sensors, such as moisture or humidity sensors, may be incorporated into the coating monitor.

Figure 3:
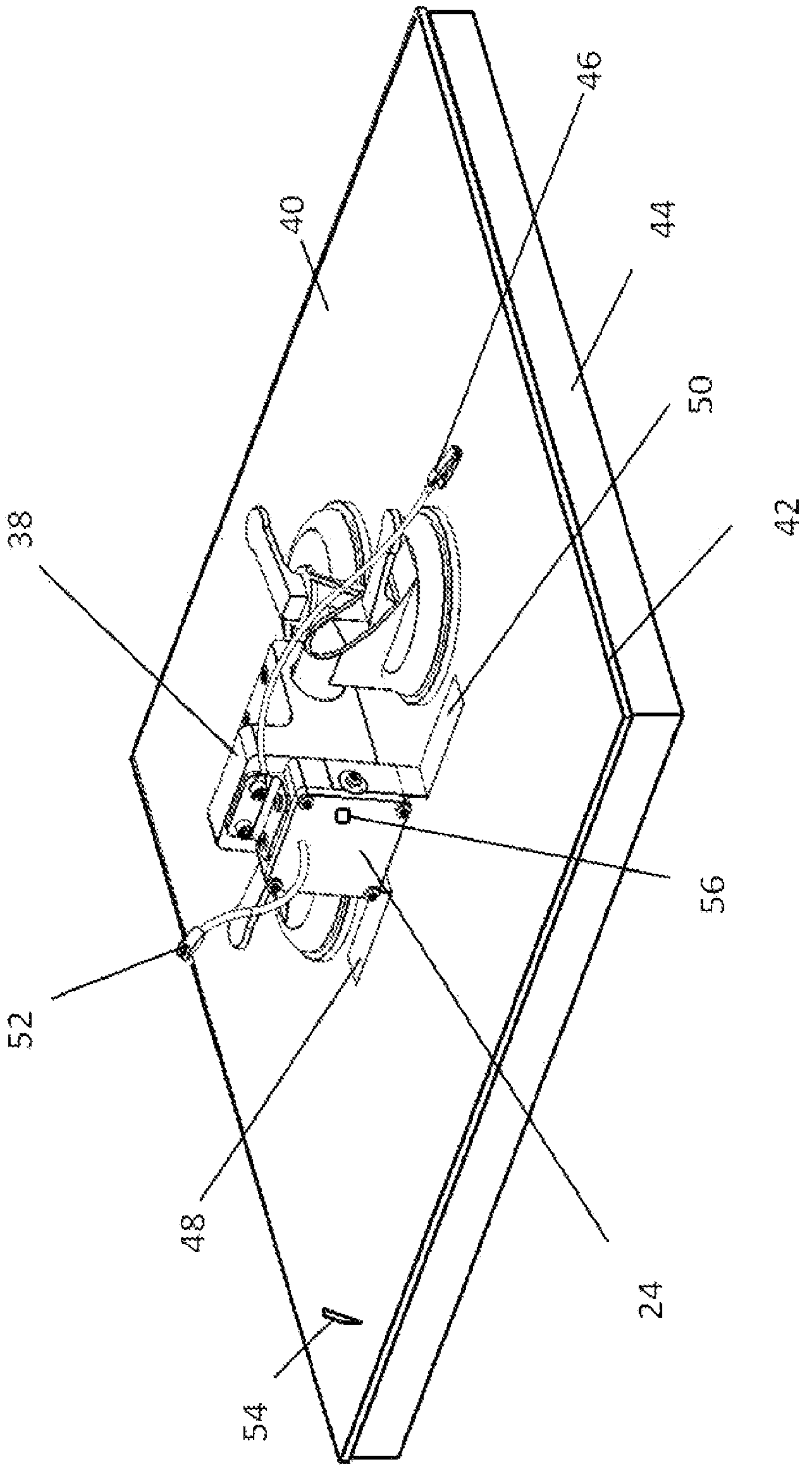
FIG. 3 shows a first embodiment of the coating monitor involving a temporary attachment.

FIG. 3 shows one embodiment of a coating monitor 24 attached with a suction cup attachment 38 to a coated structure 40. Clearly, other attachment means could be used such as mechanical fastening means, magnets, adhesives, or other means. The coating 42 would typically be applied to the substrate 44 to prevent or reduce corrosion, degradation, or other deterioration. The coating may include paints, other polymeric films, appliqués or other peel-and-stick films, ceramic coatings, conversion coatings, anodized films, or other applied, grown, or deposited coatings. The substrate could be any material that is electrically conductive for example metal, carbon-filled polymers, metal-filled polymers or any other electrically conductive material. This substrate could be a component of almost any type of structure, for example bridges, airplanes, ships, ground vehicles, tanks, pipelines, buildings, towers, supporting members or the like. The substrate could also be laboratory test panels, coupons, samples, or similar items.

In the embodiment shown in FIG. 3, the coating monitor 24 applies the ac voltage between the substrate 44, which is electrically connected to the coating monitor via lead 46 at a convenient connection point and one or more electrodes 48 and 50. These electrodes are electrically connected to the coating and comprise a flexible, electrically conductive material, preferably metal and more preferably a metallic tape with an electrically conductive pressure sensitive adhesive. The data may be stored internally to the coating monitor or may be outputted to a computer or other device in real time via lead 52. Alternatively and, in some cases preferably, the data may be wirelessly transmitted to a computer or other device. The coating monitor may have internal battery power or may obtain power via lead 52.

Figure 4:
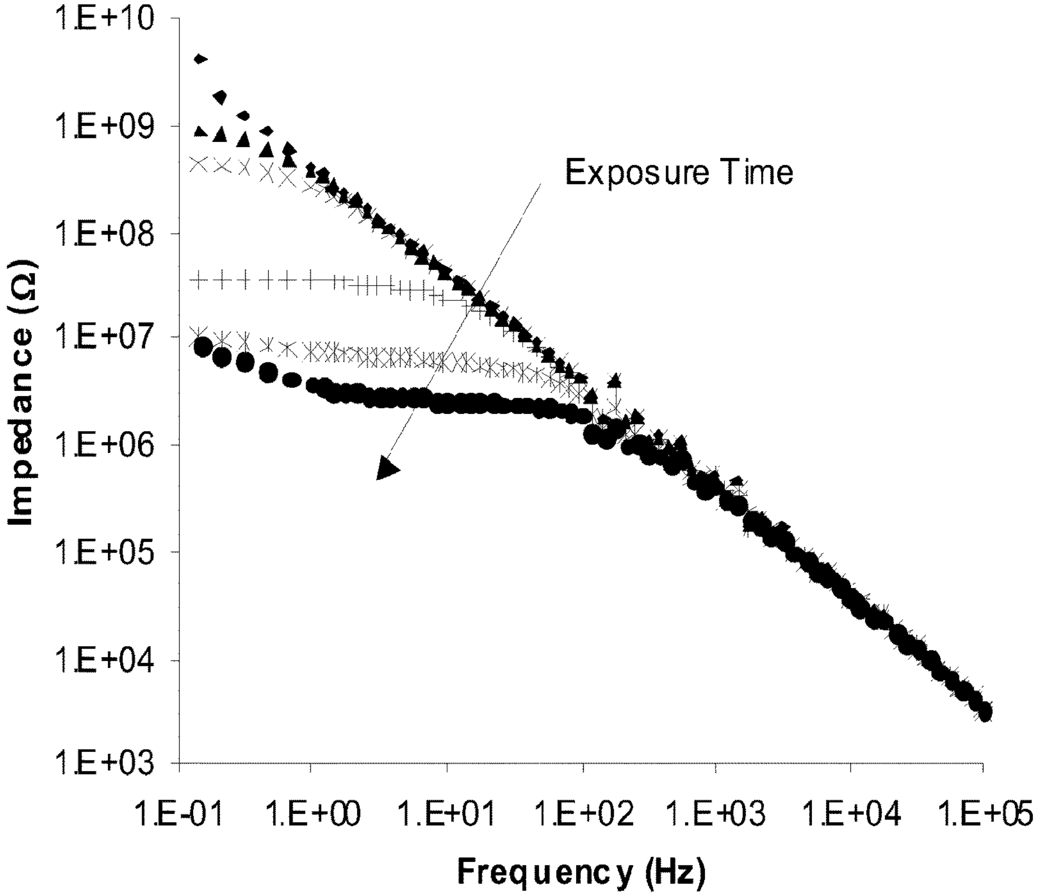
FIG. 4 shows an example of the electrochemical impedance spectrum of a coating as the coating is deteriorating.

FIG. 4 shows an example of the electrochemical impedance spectra of a painted substrate following different exposure times in an aggressive, corrosive environment. The coating monitor provides the electrochemical impedance at one or more frequencies as a function of time. As the coating degrades or deteriorates the electrochemical impedance at low frequencies decreases by several factors of ten. Because of this large change in the magnitude of the low-frequency impedance, these frequencies were chosen for the coating monitor. In the case of a coating defect 54 of FIG. 3, the electrochemical impedance can drop a similar amount with a very short exposure to the aggressive environment. The range of detection of coating defects 54 or deterioration by the coating monitor 24 depends on the coating's surface conductivity, which is commonly governed by the amount of humidity or moisture on the surface. The coating monitor 24 can provide a measure of the amount of humidity or moisture using several methods. One such method is to measure the electrochemical impedance between the two electrodes 48 and 50 instead of between one of the two electrodes 48 or 50 and the substrate 44. Another method is to measure the humidity/moisture with a humidity/moisture detector 56 mounted on or near the coating monitor 24. The electrochemical impedance of a coating is also a function of the coating thickness; accordingly, the results of the coating monitor may also be used to determine the thickness of the coating.

Figure 5:
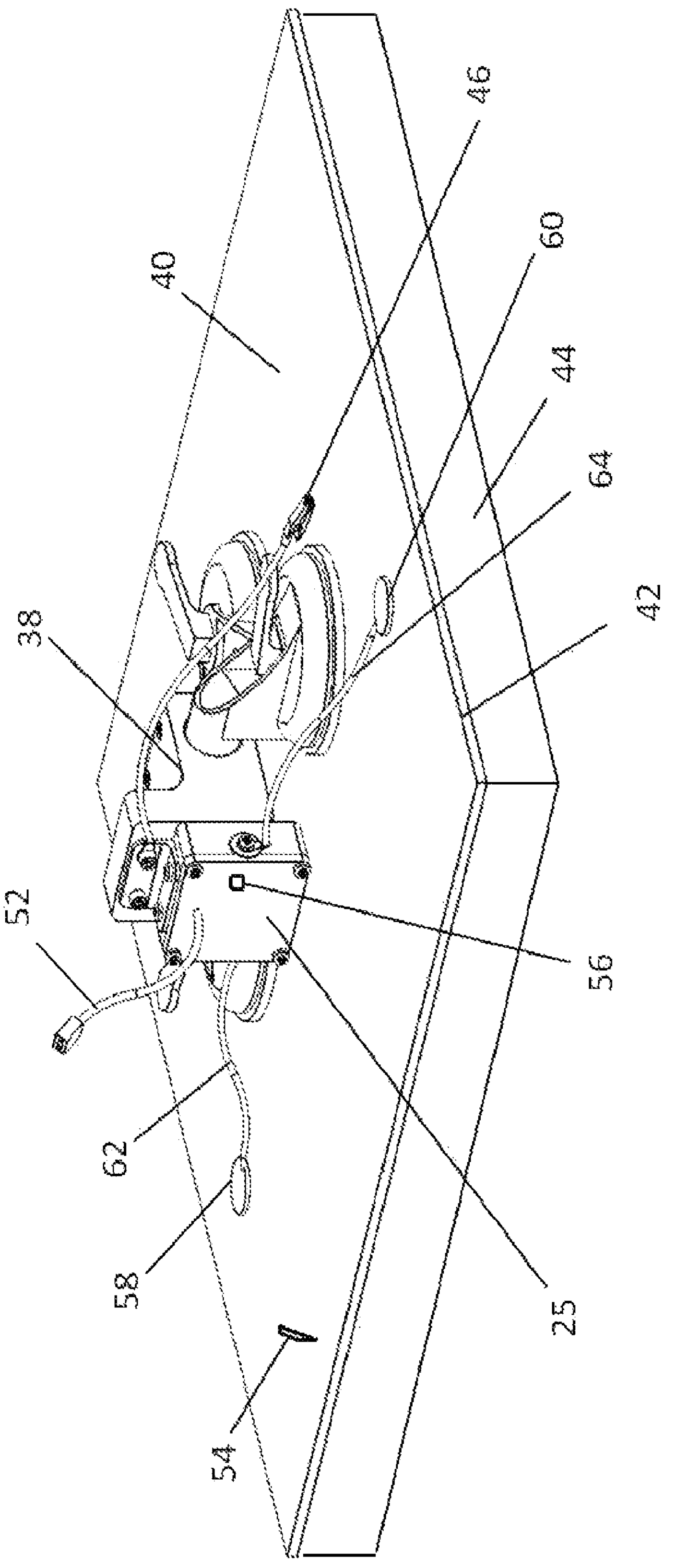
FIG. 5 shows a second embodiment of the coating monitor involving a temporary attachment.

FIG. 5 shows a second embodiment of the coating monitor 24. In this embodiment, the flexible electrodes 48 and 50 of FIG. 4 are replaced by one or more probes 58 and 60 that are electrically connected to the coating monitor 24 via leads 62 and 64. The probes comprise an electrically conductive material, preferably metal, which can be of any shape. The probes 58 and 60 may be held against the structure 40 by a variety of methods, including gravity based on the weight of the probes, electrically conductive adhesive applied to the bottom of the probes, adhesive tape applied across the probe and the structure, magnets, mechanical fasteners, suction cup apparatuses, or other means. A small amount of electrically conductive liquid may be used underneath the probes to facilitate good electrical connection to the surface of the substrate. Measurements using this embodiment proceed according to same procedure described above.

Figure 6:
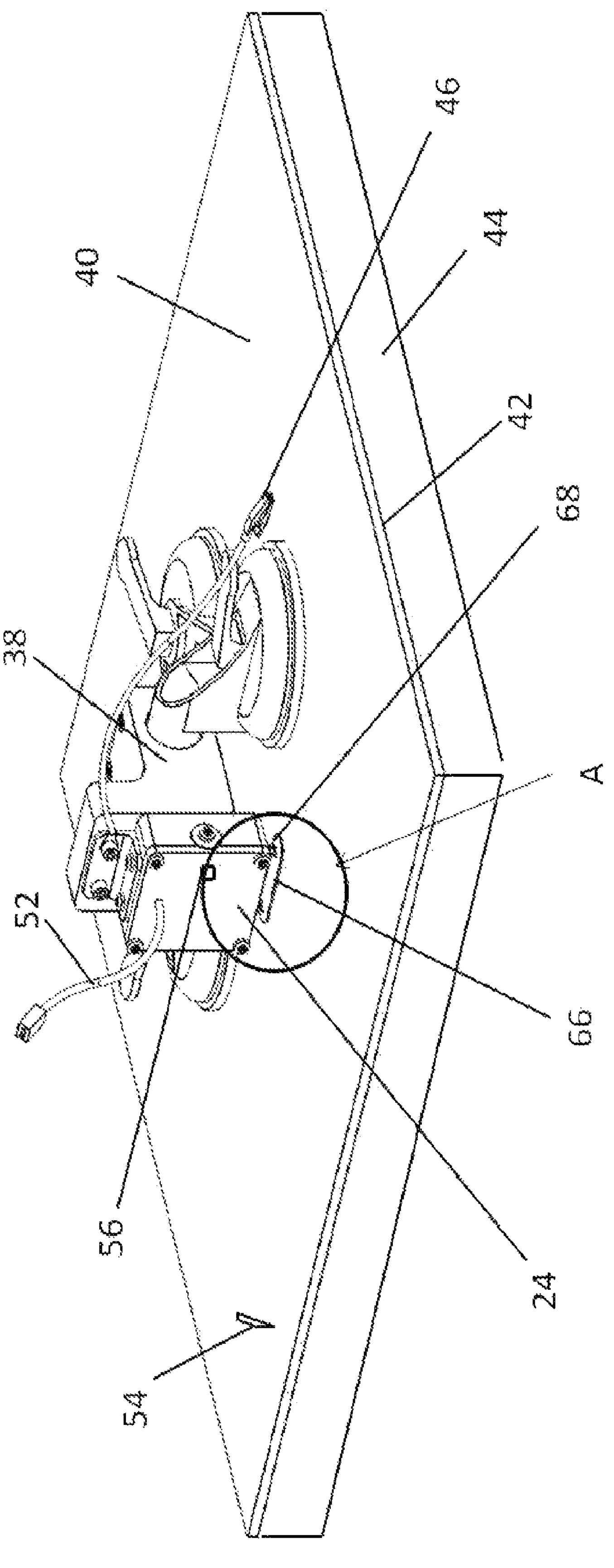
FIG. 6 shows a third embodiment of the coating monitor involving a temporary attachment.

FIG. 6 shows a third embodiment of the coating monitor 24 in which the flexible electrodes 48 and 50 as shown in FIG. 3 are replaced by one or more probes 66 that are not attached to structure 40 but are instead pressed against the structure 40 using springs 68 attached to the coating monitor. The probe(s) comprise an electrically conductive material, preferably metal, which can be of any shape. The springs provide electrical connection between the probe(s) 66 and the coating monitor 24. Alternately, the springs may be replaced with a pad or other material or device that provides a force to hold the probe(s) 66 against the structure 40. In this case, since the pad might not be a conductive material, the required electrical connections between the probe(s) 66 and the coating monitor 24 may be provided by wire leads (not illustrated). A small amount of electrically conductive liquid may be used underneath the probe(s) to facilitate good electrical connection to the surface of the structure. Measurements using this embodiment proceed according to the same procedure described above. This embodiment is useful for situations where it is not desirable to attach the probe to the structure. This situation could arise in an environment where the structure might be damaged by the attachment means. In addition, this embodiment would be useful in a fluid flow environment where anything attached to the structure would not be desired, for example on an airfoil. This embodiment also permits a single coating monitor to be used to take coating measurements in multiple locations on a structure or on multiple structures.

Figure 7:
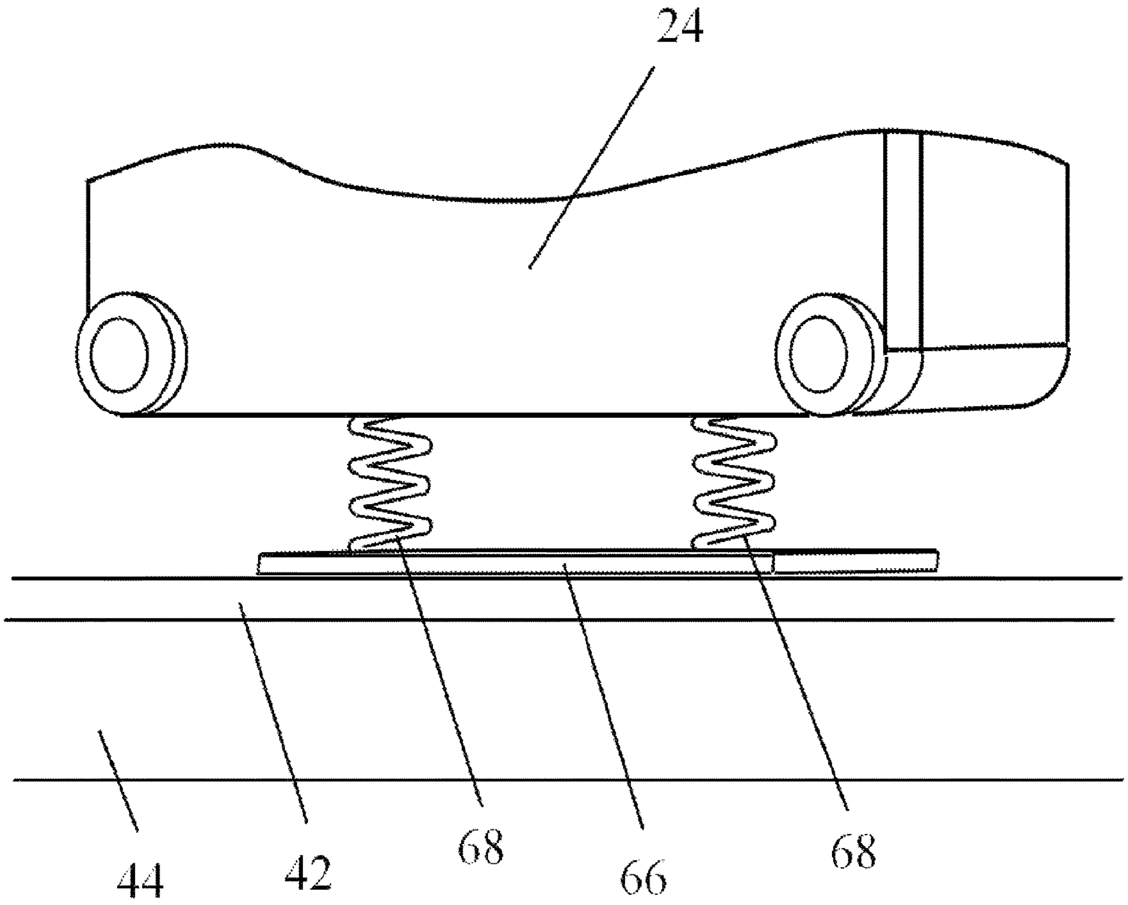
FIG. 7 shows a blown-up view of area A of FIG. 6.

FIG. 7 shows an enlarged view of area A of FIG. 6. Coating monitor 24 is mounted on coated substrate 40. Probe(s) 66 are pressed against the structure 40 by springs 68 attached to coating monitor 24. Springs 68 provide an electrical connection between probe(s) 66 and coating monitor 24.

Figure 8:
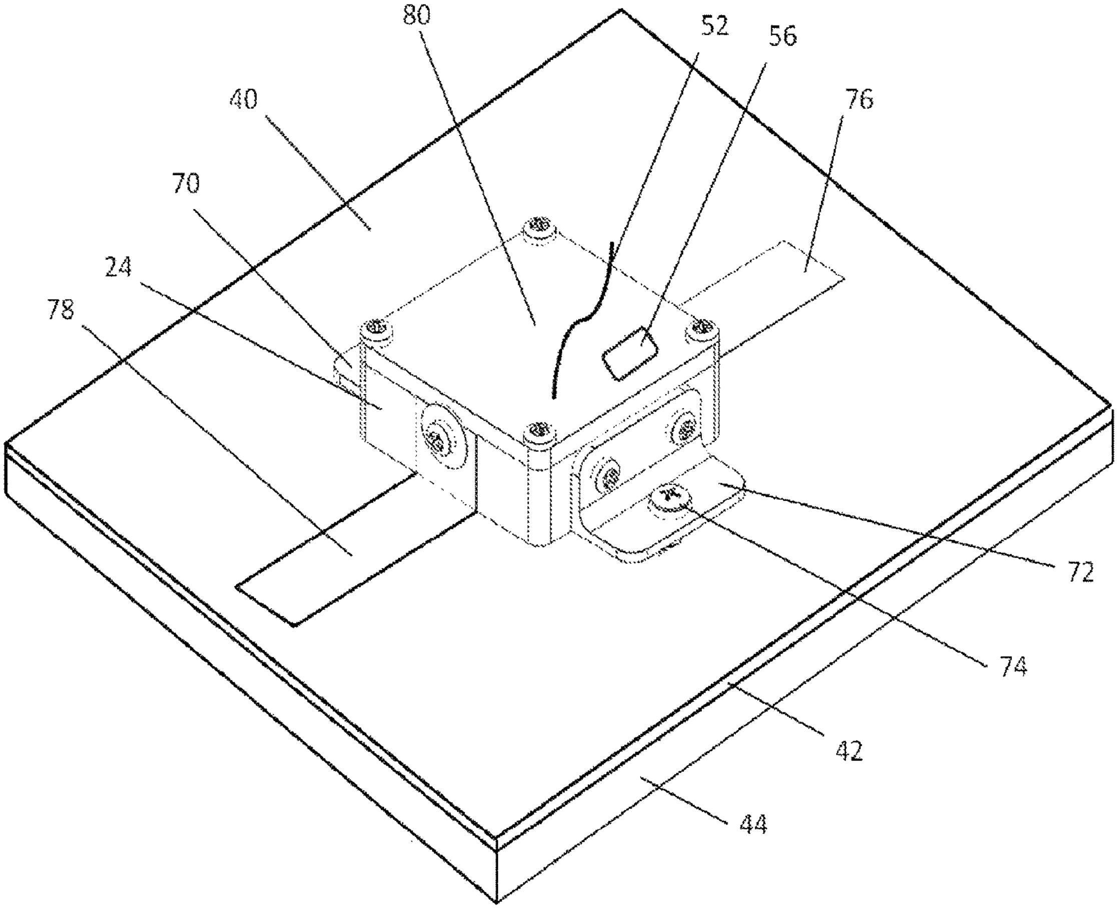
FIG. 8 shows a fourth embodiment of the coating monitor involving a permanent attachment.

FIG. 8 shows a fourth embodiment of the coating monitor 24 where it is permanently or semi-permanently attached to the structure 40 via brackets 70 and 72 and screws, rivets, or bolts 74. Other attachment methods are also possible. Electrical connection from the coating monitor to the substrate 44 is provided by the brackets and screws, rivets, or bolts. The electrodes 76 and 78 may be similar to the electrodes 48 and 50 of FIG. 3. These electrodes comprise an electrically conductive material, preferably metal and more preferably a metallic tape with an electrically conductive pressure sensitive adhesive. Alternatively, electrodes 76 and 78 may be comprised of a conductive paint or ink or a more rigid material, such as electrodes 58 and 60 (as shown in FIG. 5), or probe(s) 66 (as shown in FIG. 6). Because the coating monitor 24 may remain attached to the structure 40 for an extended period of time, the electrodes 76 and 78 preferably comprise a corrosion-resistant material that will not corrode or degrade during the expected period of operation. Alternatively, the electrodes and the coating monitor 24, brackets 70 and 72, and screws 74 may be covered with paint or other coating for corrosion protection or cosmetic, camouflage, or other reason. If the coating monitor is powered by an internal battery instead of external power via lead 52, a removable lid 80 may be provided for battery replacement. Alternative means of power may include solar cells, vibrational or other energy scavenging, or radio frequency induction to replace or supplement the battery. Battery lifetime depends on a number of factors including the frequency of measurement and the frequency of interrogation. Calculations assuming reasonable values for these parameters predict a battery lifetime of up to approximately ten years. Measurements using this embodiment, including humidity/moisture measurements proceed according to same procedure described above.

Figure 9:
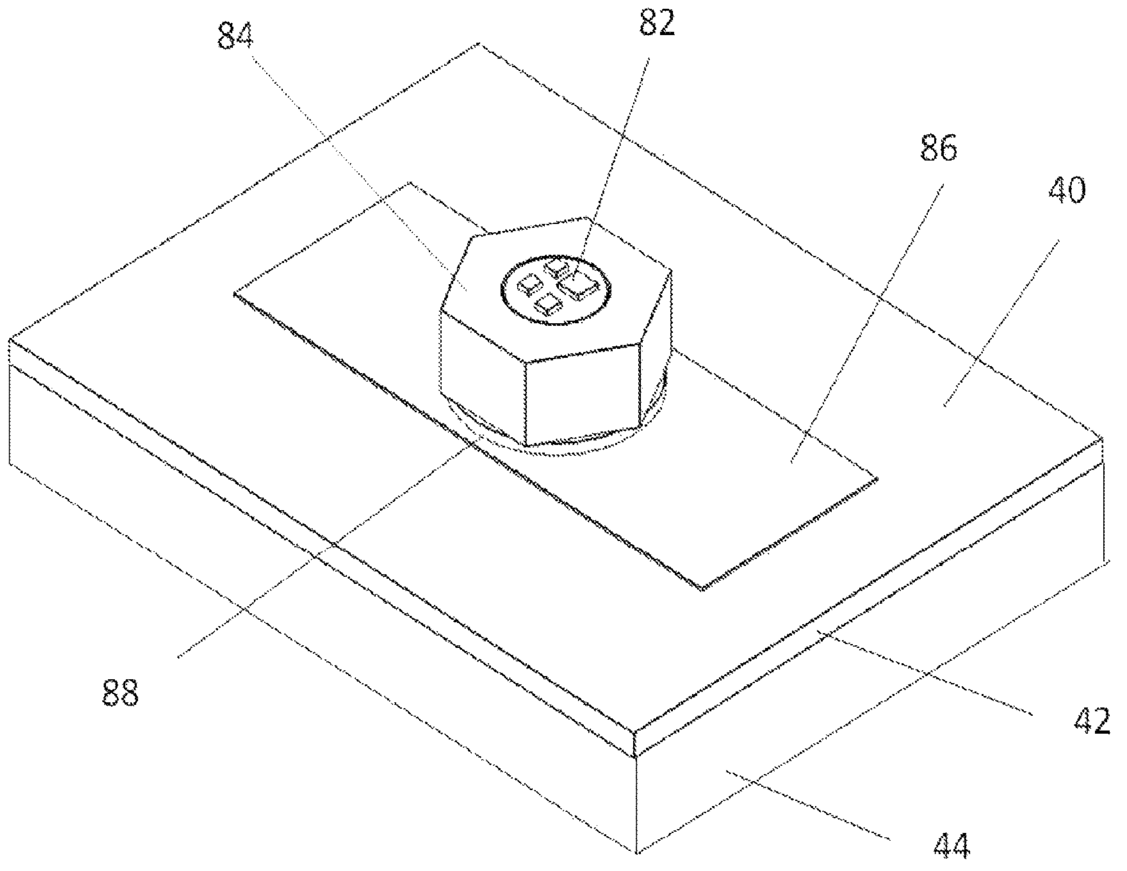
FIG. 9 shows a fifth embodiment involving an application-specific integrated circuit version of the coating monitor.

FIG. 9 shows a fifth embodiment of an application-specific-integrated-circuit version of the coating monitor. The hybrid-circuit and application-specific-integrated-circuit versions of the coating monitor provide significant reductions in size and power consumption. The coating monitor electronics 82 have been reduced in size to fit into the hollowed head 84 of a bolt. In this case, the battery (not shown) lies below the coating monitor electronics. Other configurations are also possible. The electrode 86 can be comprised of the materials of electrodes 48 and 50 (as shown in FIG. 3) or 76 and 78 (as shown in FIG. 7). Electrical connection to the substrate 44 is achieved via the threads of the bolt. An optional washer 88 allows the bolt to be tightened without damaging the electrode. In this configuration, the bolt head 84 provides electrical connection to the electrode and is electrically isolated from the threads. Other configurations are also possible.

The coating monitors may be provided with a unique number or indicator so that if a plurality of coating monitors are mounted onto a structure, readings can be obtained from each individually. Alternatively, they may be networked together so that readings from all of them may be obtained as a system. The coating monitor can be programmed to take measurements at a desired repeat frequency, for example hourly, daily, weekly, or monthly or whenever the monitor receives a signal from an inspector.

Operation:

An operator or inspector will attach, using either a temporary or (semi)permanent attachment, one or more coating monitor units to a structure. The inspector records the coating monitor identification number and location on the structure and then either begins the measurement or sets the measurement schedule. The measurement results are either transferred directly to a computer or other device or are stored until the coating monitor is interrogated. The electrochemical impedance measurement provides an indication of the health of coating or, in some cases, the coating thickness. A protective coating will exhibit a large electrochemical impedance at low frequencies while a poor coating or a good coating with a defect will exhibit a low-frequency electrochemical impedance several factors of ten smaller. Knowledge of the protectiveness of a coating can allow condition-based maintenance of a critical structure and help provide increased readiness and safety.

The invention claimed is:

1. A bolt-mounted coating monitor comprising:

a bolt comprising a head and a threaded bolt body, said bolt body further comprising an electrically conductive material, and wherein said bolt head is provided with a recess and said bolt head is electrically isolated from said bolt body;

an application-specific-integrated-circuit comprising;

an ac voltage generator operating at a plurality of frequencies below 100 Hz;

a galvanometer;

a current conversion means capable of converting current measured by said galvanometer into electrochemical impedance measurements;

an input-output means capable of storing and transferring electrochemical impedance measurements generated by said current conversion means to an external storage device, and means to make an electrical connection to a substrate;

one or more electrodes electrically connected to a portion of said bolt head and electrically connected to said application-specific-integrated-circuit;

a power supply; wherein said application-specific-integrated-circuit and said power supply are mounted in said recess; and, wherein said means to make an electrical connection to a substrate is electrically connected to said threaded bolt body.

2. The bolt-mounted coating monitor of claim 1 wherein said galvanometer measures both current magnitude and current phase.

3. The bolt-mounted coating monitor of claim 1 further comprising moisture detecting means.

4. The bolt-mounted coating monitor of claim 1 wherein said ac voltage generator operates at a plurality of frequencies below 10 Hz.

5. The bolt-mounted coating monitor of claim 4 further comprising a washer placed between said portion of said bolt head and said electrode.

6. The bolt-mounted coating monitor of claim 1 wherein the power supply further comprises an energy scavenging apparatus.

7. The bolt-mounted coating monitor of claim 1 wherein the power supply further comprises a battery.

8. The bolt-mounted coating monitor of claim 7 wherein the power supply further comprises an energy scavenging apparatus supplementing the battery.

9. The bolt-mounted coating monitor of claim 8 wherein the energy scavenging apparatus further comprises a vibration energy scavenging apparatus.

10. The bolt-mounted coating monitor of claim 1 wherein the power supply further comprises a solar cell apparatus.

* * * * *